US012636591B2

(12) United States Patent
Becker et al.

(10) Patent No.: US 12,636,591 B2
(45) Date of Patent: May 26, 2026

(54) FACILITY AND METHOD FOR PURIFYING RECOVERED NMP

(71) Applicant: GEA WIEGAND GMBH, Ettlingen (DE)

(72) Inventors: Jörg Becker, Karlsruhe (DE); Ralf Leibig, Hambrücken (DE)

(73) Assignee: GEA Wiegand GmbH, Ettlingen (DE)

( * ) Notice: Subject to any disclaimer, the term of this patent is extended or adjusted under 35 U.S.C. 154(b) by 279 days.

(21) Appl. No.: 18/562,464

(22) PCT Filed: May 16, 2022

(86) PCT No.: PCT/EP2022/063174
§ 371 (c)(1),
(2) Date: Nov. 20, 2023

(87) PCT Pub. No.: WO2022/243238
PCT Pub. Date: Nov. 24, 2022

(65) Prior Publication Data
US 2024/0238693 A1 Jul. 18, 2024

(30) Foreign Application Priority Data
May 21, 2021 (EP) ..................................... 21175251

(51) Int. Cl.
*B01D 3/14* (2006.01)
*B01D 1/28* (2006.01)
(Continued)

(52) U.S. Cl.
CPC ........... *B01D 3/148* (2013.01); *B01D 1/2856* (2013.01); *B01D 5/006* (2013.01); *C07D 207/267* (2013.01)

(58) Field of Classification Search
CPC ...... B01D 3/148; B01D 1/2856; B01D 5/006; B01D 3/143; C07D 207/267
See application file for complete search history.

(56) References Cited

U.S. PATENT DOCUMENTS

2009/0326307 A1 12/2009 Panditrao et al.
2012/0241307 A1 9/2012 Miyata et al.
(Continued)

FOREIGN PATENT DOCUMENTS

CN 108654130 A 10/2018
JP 2009212426 A 9/2009

OTHER PUBLICATIONS

International Application No. PCT/EP2022/063174, International Search Report and Written Opinion mailed Sep. 8, 2022, 14 pages.

*Primary Examiner* — Renee Robinson
(74) *Attorney, Agent, or Firm* — Kilpatrick Townsend & Stockton LLP

(57) ABSTRACT

The present invention relates to a facility for purifying recovered NMP from lithium-ion battery production, comprising a first column for separating low-boiling impurities, comprising a supply, in its central part, for the recovered NMP, and which can be heated by means of a first evaporator for supplying thermal energy; and a second column for separating high-boiling impurities, a connection line from a lower part of the first column to a lower part of the second column being provided. In this case, according to the invention, the second column (38) can be heated by means of a second evaporator comprising an inlet and an outlet for purified NMP, and the second column is assigned a compressor portion which extends from a head of the second column to the inlet of the second evaporator and comprises a mechanical vapor compressor for inputting energy to the vapor of the second column. The present invention furthermore relates to a method for operating a facility of this kind.

14 Claims, 2 Drawing Sheets

Figure 1:
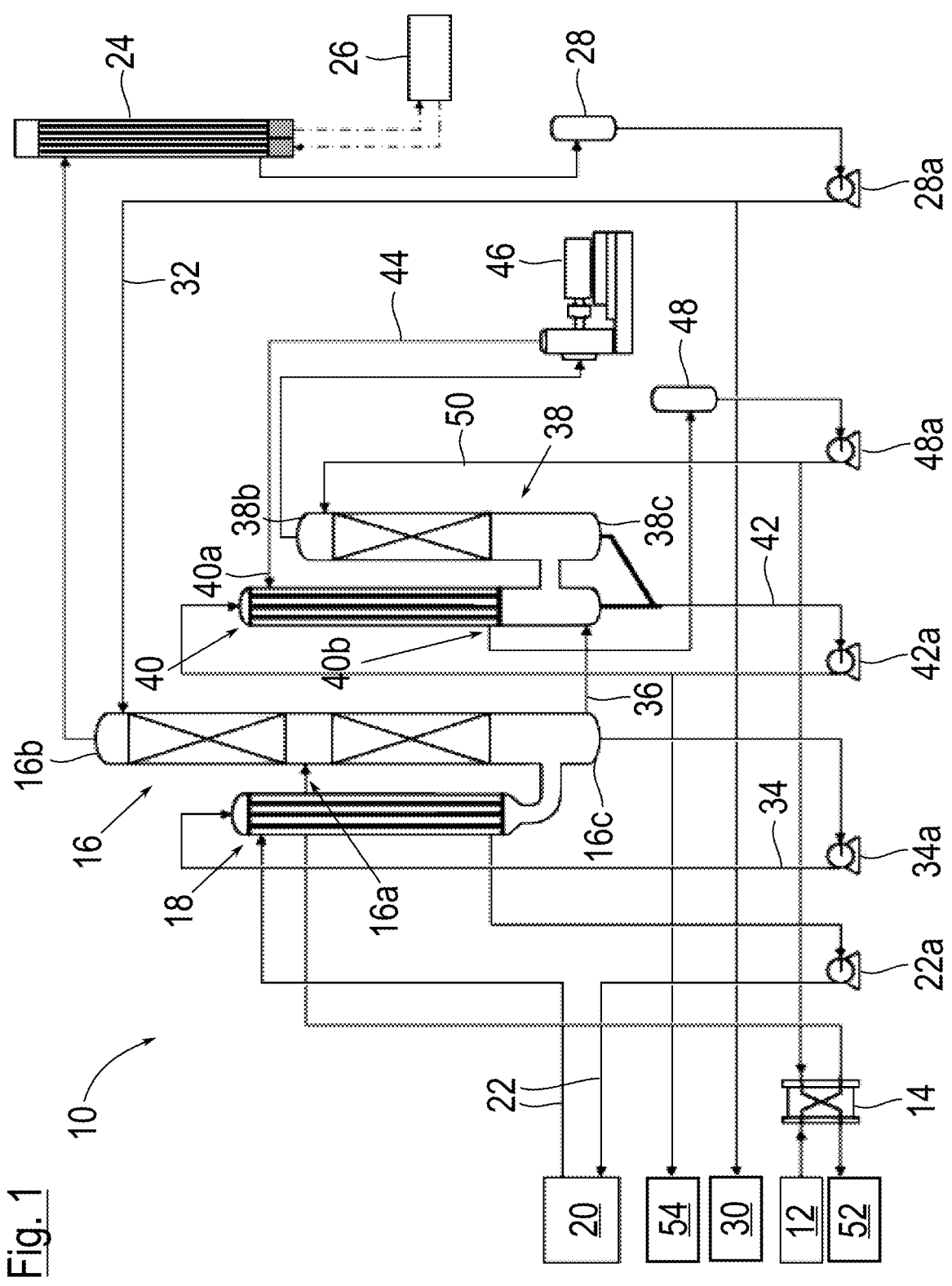

(51) Int. Cl.
    *B01D 5/00*        (2006.01)
    *C07D 207/267*    (2006.01)

(56)           References Cited

U.S. PATENT DOCUMENTS

| | | | |
|---|---|---|---|
| 2013/0267751 A1 | 10/2013 | Favilli et al. | |
| 2014/0339069 A1* | 11/2014 | Maedebach | B01D 3/007 |
| | | | 202/159 |
| 2015/0052940 A1 | 2/2015 | King et al. | |
| 2018/0185766 A1 | 7/2018 | King et al. | |
| 2020/0179820 A1 | 6/2020 | Kim et al. | |

\* cited by examiner

FACILITY AND METHOD FOR PURIFYING RECOVERED NMP

CROSS REFERENCE TO RELATED APPLICATIONS

This application is a U.S. national phase of International Patent Application No. PCT/EP2022/063174 filed on May 16, 2022, which claims priority to European Patent Application No. 21175251.4, filed in Europe on May 21, 2021. The entire contents of both applications are hereby incorporated herein by this reference.

The present invention relates to a facility for purifying recovered NMP from lithium-ion battery production, and to a method for purifying recovered NMP by means of a facility of this kind.

In particular in the case of manufacture of electrodes for lithium-ion batteries, NMP (N-Methyl-2-pyrrolidone) of particularly high quality is required as the solvent. The NMP used is then vaporized out of the electrode material in a drying installation and subsequently condensed, in order to be recovered for re-use.

Due to the method, the recovered condensed NMP, which has a boiling point of approximately 200° C. under normal conditions, contains both low-boiling impurities, for example water, and high-boiling impurities, for example residues of electrode material.

Various methods for purifying the recovered NMP are known, reference being made for example to JP 2009 212 426 A, in which, in a two-stage process, firstly low-boiling impurities are separated in a first column, whereupon the pre-purified NMP is then itself separated from the high-boiling impurities in a second column. In the mentioned example, the energy required for the purification is introduced into the two columns by means of thermal energy, for example steam or heat transfer fluid.

In this case, however, it is found that this type of energy input results in high energy consumption and high running costs during operation of the corresponding facility. There is therefore potential for improvement with regard to the energy efficiency and the operating costs of facilities and methods known from the prior art for purification of recovered NMP from lithium-ion battery production.

The possibility of reducing thermal energy by using heat pump technology is made more difficult firstly by the very high temperature difference of over 80 Kelvin between the condensation temperature of the overhead product (in particular the boiling temperature of water) and the evaporation temperature of the NMP in the bottom of the column.

In this case, it should be noted in addition that, due to the method, the NMP typically accumulates, upon recovery, with a water or low boiler fraction of less than 5%, as a result of which only a small portion of energy has to be used for depletion of the low boilers during purification of the NMP, while the majority of the energy is required for vaporizing the NMP or for high boiler separation in a second process step.

Accordingly, the object of the present invention is that of developing known facilities and methods for purifying recovered NMP in a manner which allows for increased energy efficiency and more cost-effective operation.

For this purpose, a facility according to the invention for purifying recovered NMP from lithium-ion battery production comprises a first column for separating low-boiling impurities, comprising a supply, in its central part, for the recovered NMP, and which can be heated by means of a first evaporator for supplying thermal energy, and a second column for separating high-boiling impurities, a connection line from a lower part of the first column to a lower part of the second column being provided. According to the invention, in this case the second column can be heated by means of a second evaporator, comprising an inlet and an outlet for purified NMP, by condensation of the purified NMP vapor, and the second column is assigned a compressor portion which extends from a head of the second column to the inlet of the second evaporator and comprises a mechanical vapor compressor for increasing the pressure and thus increasing the condensation temperature of the purified NMP vapor of the second column.

According thereto, the mode of operation of the facility according to the invention is based on introducing a portion of the energy, required for purifying the supplied NMP, by means of mechanical vapor compression according to the heat pump principle. In this case, in order to achieve the required product purity an arrangement has been selected in which the two separation tasks, specifically low boiler separation and high boiler separation, are divided over two columns. This results, for the second separation task, i.e. the high boiler separation, in a significantly reduced temperature difference between the condensation temperature of the overhead product, specifically the purified NMP, and the evaporation temperature of the NMP contaminated with high boilers, in the bottom of the column.

In this way, in particular the use of mechanical vapor compression is suitable for said second separation task, and having a coefficient of performance, defined as thermal heating power divided by electrical power of the mechanical vapor compression of approximately 20 in practical operation, a significantly increased energy efficiency can be achieved in this separation task, compared with the known methods described above.

In this case, a significant factor is that, for this second separation task, the complete NMP including the required return flow has to be vaporized, and more than 80% of the total energy of the operation of the entire facility according to the invention has to be used for this purpose. Thus, in view of the above-mentioned coefficient of performance that is achievable in practice an energy saving in the overall facility of up to 75% can be achieved by the use of the mechanical vapor compression, as a result of which the installation and the operation of the mechanical vapor compressor can be amortized in just a short time.

In order to further increase the efficiency of the facility, a heat exchanger, in particular a plate heat exchanger, can be connected upstream of the supply of the first column, which heat exchanger is also coupled to the outlet of the second evaporator. As a result, the recovered NMP removed from the facility can emit a further portion of its heat, absorbed during the process, to the NMP to be recovered that is to be supplied, as a result of which the corresponding energy remains in the facility and accordingly does not have to be additionally delivered or is not lost.

Furthermore, alternatively or in addition the facility according to the invention can further comprise a condenser for condensing the low-boiling impurities, which condenser is coupled to the head of the first column. The condensate produced in this way can be removed from the facility as a waste product, and can also be returned, in part, into the first column as a return flow.

Since said condenser represents the point in the facility at which the lowest pressure prevails, it can furthermore be assigned a vacuum pump, which is designed to maintain and adjust a pressure, in the facility, that is reduced compared with the surroundings. Since it must always be anticipated, in such complex facilities, that ambient air can penetrate at various points, via minimal leak points, said vacuum pump is required in order to achieve a reduction in the operating temperature and thus a further energy saving compared with normal conditions.

Various designs of downflow evaporators or circulation evaporators are particularly suitable for use as the first and/or the second evaporator, while, however, in principle the use of other evaporator types is also conceivable at this point for inputting the heat, required for the corresponding processes, into the facility.

Furthermore, in one embodiment of the facility according to the invention, a vapor recovery line can be provided between the lower part of the first column and the lower part of the second column, and a vent line comprising a control valve can be provided between the second evaporator and a central portion of the first column. Providing the vapor recovery line achieves pressure and temperature compensation between the lower parts of the first and second column, while a suitable pressure gradient at the corresponding points of the facility can be set by the vent line.

Providing these additional components in a facility according to the invention is advantageous in a number of ways. Firstly, excess thermal energy of the second evaporator heated by means of the mechanical vapor compressor can be coupled into the thermally heated first column, as a result of which the need for an additional device, such as in particular an additional condenser downstream of the second evaporator, or a cooler, can be dispensed with. Secondly, venting of inert gases via downstream systems can be omitted, which would also require additional devices and is associated with the risk of spreading of traces of non-separated low boilers into the product due to complete condensation, in that partial condensation, controlled by the vent line, is carried out in the second evaporator, and the vent vapor of said second evaporator is coupled, in this way, into the first column. Lastly, providing the vapor recovery line makes it possible, in particular during startup of the facility, for the heating device of the first column to be used for heating through the second evaporator, since at this time no energy can yet be input into the facility by the mechanical vapor compressor. Therefore, here, too, the need for a further device, in particular a thermally heated preheater of the second evaporator, is dispensed with.

Furthermore, in the facility according to the invention the first column can comprise a cup outlet, from which the connection line extends to the lower part of the second column. As a result, the output of the first column is conducted out into the second column, heated by mechanical vapor compression, before it enters the column bottom of said first column. Thus, the NMP can be purified of the low-boiling impurities, in the first column, with only insignificant concentration increase of the high-boiling impurities.

In this connection, the facility can further comprise a fluid return which is designed to input high-boiling impurities, removed from the bottom of the second column, into a lower part of the first column, at least in part. Accordingly, the high-boiling impurities in the bottom of the first column can be concentrated with supply of thermal energy, which makes it possible to keep the part of the facility heated by the mechanical vapor compressor free of harmful influences caused by high concentrations of high boilers, in order to minimize the product loss with the least possible outlay in terms of apparatus, by concentration of the high-boiling impurities. In this case, an embodiment of this kind is suitable in particular for high-boiling impurities having low vapor pressure, i.e. for example residues of electrode material.

Furthermore, as a result of the mentioned measures, an increase in boiling point and an associated increased power requirement of the vapor compressor is omitted by a reduced concentration of the high-boiling impurities in the part of the facility heated by the mechanical vapor compressor. Furthermore, it is also possible to omit an evaporator assigned to the vapor compressor, which could possibly be necessary at this point on account of possibly precipitating solids, an increased viscosity, and worse heat transfer.

In order to remove the high-boiling impurities from the facility, in such embodiments, said facility can further comprise a discharge line for conducting high-boiling impurities out of the lower part of the first column to a removal line.

As already indicated, according to a second aspect the present invention relates to a method for purifying recovered NMP from lithium-ion battery production, by means of a facility according to the invention of the type just described, comprising the steps of:

inputting the recovered NMP into the central part of the first column;

heating the first column by means of the first evaporator by supplying thermal energy;

removing low-boiling impurities from the head of the first column;

transferring pre-purified NMP from the lower part or the cup outlet of the first column into the lower part of the second column;

vaporizing the pre-purified NMP in the second evaporator and conducting it through the second column;

removing the vaporous NMP at the head of the second column and compressing it in the compressor portion by means of the mechanical vapor compressor;

inputting the compressed NMP into the inlet of the second evaporator, the NMP condensing in the second evaporator;

removing the condensed NMP at the outlet of the second evaporator; and removing high-boiling impurities out of the bottom of the second column.

In this case, for the reasons set out above, a significant saving in energy and operating costs during operation of the facility can be achieved by the method according to the invention.

Furthermore, in order to reduce the operating temperature, and thus to further save energy, a reduced pressure, in particular of less than 100 mbar absolute pressure, can be maintained in the first and the second column.

Even if the manner of supply of thermal energy to the first evaporator can be brought about by means of any techniques, in the context of the present invention, this can take place in particular by means of steam or a heat transfer fluid, in order to be able to achieve the high heating temperature, already mentioned, for operating the first column.

Furthermore, during operation of the facility according to the invention, according to the method proposed here a portion of the condensed NMP from the second evaporator can be returned, as a return flow, into the second column.

As already indicated above, the low-boiling impurities removed from the head of the first column can furthermore be condensed in the condenser and preferably returned, at least in part, into the first column as a return flow.

While, on account of the method, the recovered NMP can typically contain less than 5% of low-boiling impurities, furthermore, in the first column the low-boiling impurities in the pre-purified NMP can be depleted to less than 0.1%, preferably less than 0.05%, in order to be able to achieve the required product quality for the purified NMP ultimately removed from the facility.

In the embodiment of a facility according to the invention already discussed above, comprising a fluid return from the bottom of the second column to the lower part of the first column, accordingly the high-boiling impurities removed from the bottom of the second column can further be input, at least in part, into the lower part of the first column, in order to achieve the advantages, also discussed above, during operation of the facility.

In particular, in such embodiments, the concentration of the high-boiling impurities in the bottom of the second column during operation of the facility, based on the initial concentration in the recovered NMP, can be approximately 1 to 5, and the concentration of the high-boiling impurities in the lower part of the first column can be increased relative to this value and can be in the range of greater than 1 to approximately 100. In a process that is particularly advantageous in terms of energy, in this case the two mentioned values are approximately 3 and in the range of 50 to 60, respectively.

Figure 2:
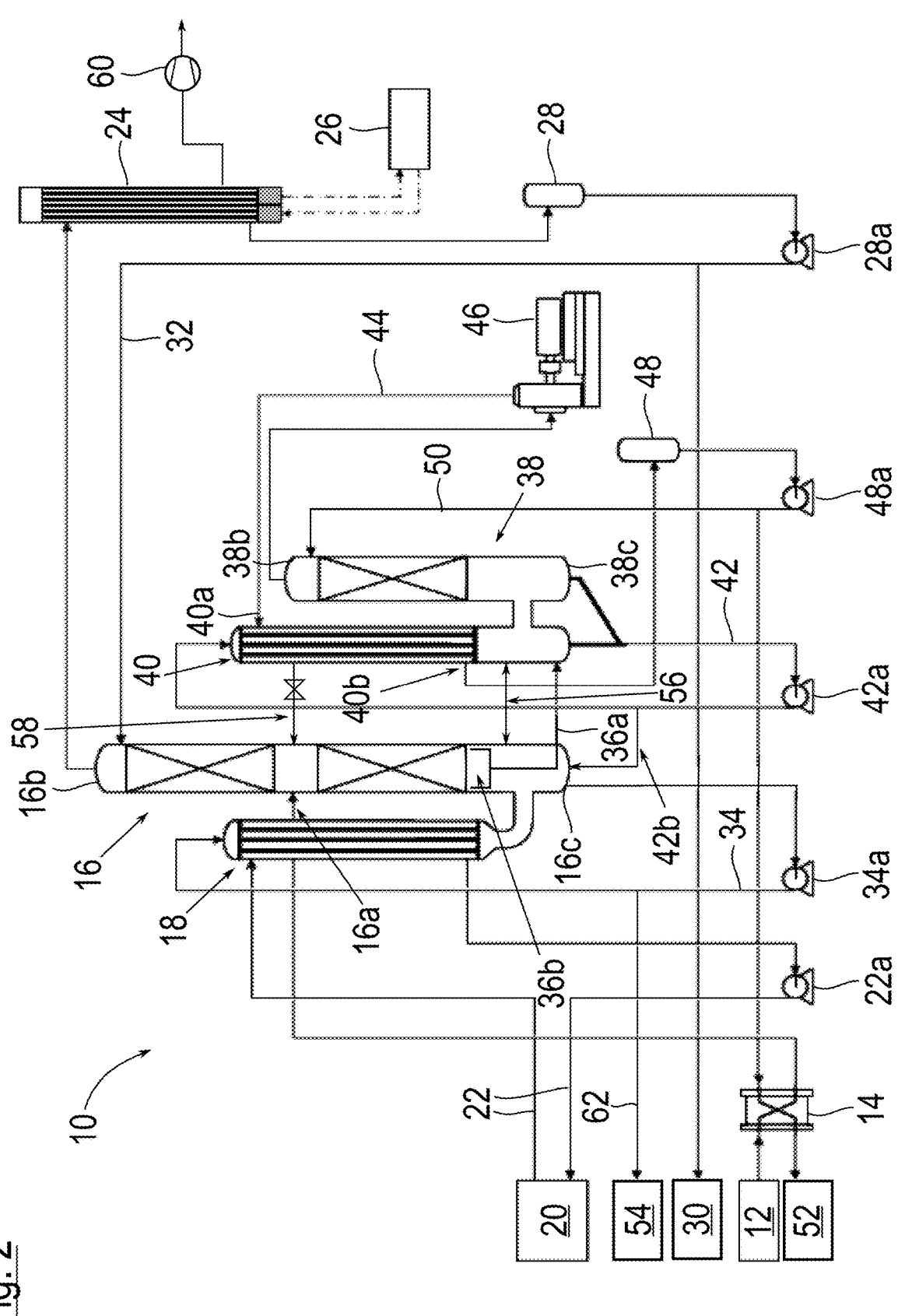

Further features and advantages of the present embodiment will become clearer from the following description of an embodiment, when viewed together with the accompanying drawings, in which, in detail:

FIG. 1 is a schematic view of a facility according to the invention for purifying recovered NMP; and FIG. 2 is a schematic view of a further variant of a facility according to the invention.

In FIG. 1, the facility according to the invention for purifying recovered NMP is denoted very generally by reference sign 10. In this case, firstly, at point 12, recovered NMP from lithium-ion battery production is input into the facility, which typically contains less than 5% low-boiling impurities, in particular water, and, additionally, high-boiling impurities, such as remaining electrode material.

In the facility 10, the NMP input into the facility firstly passes through a heat exchanger 14, in which it is pre-heated, before it is input, at point 16a, into the central part of a first column 16. In this case, the first column 16 is assigned a first evaporator 18 which can be supplied, from point 20, with steam or heat transfer fluid, for operation, by means of a circuit 22 which is driven by a pump 22a. Due to the supply of thermal energy into the first column 16 by means of the first evaporator 18, the low-boiling impurities of the supplied NMP to be recovered vaporize there, and can be removed at the head region 16b in the first column and supplied to a condenser 24 in which condensation of the low-boiling impurities is achieved by means of water cooling 26. Said condensed impurities can subsequently be collected in a tank 28 and removed from the facility, as a waste product, at point 30 by means of a pump 28a, and be returned in part into the first column 16 as a return flow, via a return line 32.

In contrast, on the lower part 16c of the first column a circulation loop 34 having a pump 34a for supplying pre-purified NMP, removed there, to the first evaporator 18 is provided, and in addition a connection line 36 is provided, via which the pre-purified NMP can be transferred from the lower part 16c of the first column 16 into the lower part 38c of a second column 38. The second column 38 can be operated in such a way as to separate the already pre-purified NMP from high-boiling impurities, in that the NMP itself vaporizes and is removed in the head region 38b of said second column 38.

For this purpose, said second column 38 is assigned a second evaporator 40 which is supplied, by means of a circuit 42a driven by a pump 42a, with bottom product that is removed from the lower part 38c of the second column 38 and has a concentration of high-boiling impurities, while in addition the vapor removed in the head region 38b of the second column 38, i.e. vaporized purified NMP, is supplied for heating the second evaporator 40. Said vapor was compressed, in the meantime, by means of a mechanical vapor compressor 46, in a compressor portion 44 extending from the head region 38b of the second column 38 to the corresponding inlet 40a of the second evaporator 40, and thus its energy content and condensation temperature were increased, as a result of which the energy required for the operation of the second column 38 is input in this way.

When passing through the second evaporator 40, which can be designed for example as a downflow evaporator or circulation evaporator, which furthermore also applies for the first evaporator 18, the purified NMP condenses and can subsequently be transferred from an outlet 40b of the second evaporator 40 into a tank 48. From there, it can subsequently be returned into the second column 38, as a return flow, by means of a pump 48a via a return line 50, and also removed from the facility 10 as an end product via an outlet line 52.

Subsequently, upon passing through the heat exchanger 14, already discussed above, the purified and condensed NMP can subsequently emit further heat to the NMP that is to be recovered and is newly supplied at point 12.

In the facility 10 according to the invention, according to the invention the use of the mechanical vapor compressor 46 for heating the second evaporator 40 achieves a significant energy saving during operation, for the sake of completeness reference finally being made again to the removal line 54, by means of which the high-boiling impurities can also be removed from the facility 10, as a waste product, from the lower part 38c of the second column 38, which impurities, as discussed above, are in part circulated into the second evaporator 40 as a return flow.

In contrast, FIG. 2 shows a further variant of a facility according to the invention, which differs from the embodiment shown in FIG. 1 with respect to a few advantageous structural features, which will be discussed in the following, while a repeated description of identical components will be omitted.

Firstly, in this variant the first column 16 comprises a cup outlet 36b, from which a connection line 36a extends to the lower part 38c of the second column 38. In this variant, this arrangement replaces the simple connection line 36 according to the first embodiment and also extends, within the meaning of the present invention, from the lower part 16c of the first column 16 to the lower part 38c of the second column 38.

Furthermore, a fluid return 42b is provided, which is designed to input high-boiling impurities, removed from the bottom 38c of the second column 38, into the lower part 16c of the first column 16, at least in part. Since, according thereto, in this variant concentration of the high-boiling impurities occurs in the lower part 16c of the first column 16, a discharge line 62 is furthermore provided, which makes it possible to conduct high-boiling impurities out of the lower part 16c of the first column 16 to the removal line 54.

Furthermore, in the variant shown in FIG. 2, a connection between the lower part 16c of the first column 16 and the lower part 38c of the second column 38 is created by a vapor recovery line 56, and at the same time a vent line comprising a control valve 58 is provided between an upper part of the second evaporator 40 and a central portion of the first column 16.

Finally, reference is also made to the vacuum pump 60, which is assigned to the condenser 24 and accordingly allows for generation and setting of a reduced pressure in the facility at the point of the facility 10 according to FIG. 2 at which a minimum pressure prevails.

The invention claimed is:

1. Facility for purifying recovered NMP from lithium-ion battery production, the facility comprising:
    a first column for separating low-boiling impurities, comprising a supply, in its central part, for the recovered NMP, and which can be heated by means of a first evaporator for supplying thermal energy; and
    a second column for separating high-boiling impurities, a connection line from a lower part of the first column to a lower part of the second column being provided;
wherein the second column can be heated by means of a second evaporator comprising an inlet and an outlet for purified NMP, and
the second column is assigned a compressor portion which extends from a head of the second column to the inlet of the second evaporator and comprises a mechanical vapor compressor for inputting energy to the vapor of the second column, and
wherein a vapor recovery line is provided between the lower part of the first column and the lower part of the second column, and a vent line comprising a control valve is provided between the second evaporator and a central portion of the first column.

2. Facility according to claim 1,
wherein a heat exchanger is connected upstream of the supply of the first column, which heat exchanger is also coupled to the outlet of the second evaporator.

3. Facility according to claim 1,
further comprising a condenser for condensing the low-boiling impurities, which condenser is coupled to the head of the first column.

4. Facility according to claim 3,
wherein the condenser is assigned a vacuum pump which is designed for maintaining a reduced pressure in the facility.

5. Facility according to claim 1,
wherein the first and/or the second evaporator is/are designed as a downflow evaporator or a circulation evaporator.

6. Facility for purifying recovered NMP from lithium-ion battery production, the facility comprising:
    a first column for separating low-boiling impurities, comprising a supply, in its central part, for the recovered NMP, and which can be heated by means of a first evaporator for supplying thermal energy; and
    a second column for separating high-boiling impurities, a connection line from a lower part of the first column to a lower part of the second column being provided;
wherein the second column can be heated by means of a second evaporator comprising an inlet and an outlet for purified NMP, and
the second column is assigned a compressor portion which extends from a head of the second column to the inlet of the second evaporator and comprises a mechanical vapor compressor for inputting energy to the vapor of the second column, and wherein the first column comprises a cup outlet, from which a connection line extends to the lower part of the second column.

7. Facility according to claim 6,
further comprising a fluid return which is designed to input high-boiling impurities, removed from a bottom of the second column, into a lower part of the first column, at least in part.

8. Facility according to claim 7,
further comprising a discharge line for conducting high-boiling impurities out of the lower part of the first column to a removal line.

9. Method for purifying recovered NMP from lithium-ion battery production, by means of a facility according to claim 1, comprising the steps of:
    inputting the recovered NMP into the central part of the first column;
    heating the first column by means of the first evaporator by supplying thermal energy;
    removing low-boiling impurities at the head of the first column;
    transferring pre-purified NMP from the lower part of the first column or a cup outlet into the lower part of the second column;
    vaporizing the pre-purified NMP in the second evaporator and conducting it through the second column;
    removing the vaporous NMP at the head of the second column and compressing it in the compressor portion by means of the mechanical vapor compressor;
    inputting the compressed NMP into the inlet of the second evaporator, wherein the NMP condenses in the second evaporator;
    removing the condensed NMP at the outlet of the second evaporator; and
    removing high-boiling impurities out of the bottom of the second column, wherein the high-boiling impurities removed from the bottom of the second column are input into a lower part of the first column, at least in part.

10. Method according to claim 9,
wherein a reduced pressure is maintained in the first and the second column.

11. Method according to claim 9,
wherein the supply of thermal energy to the first evaporator takes place by means of steam or a heat transfer fluid.

12. Method according to claim 9,
wherein a portion of the condensed NMP from the second evaporator is returned, as a return flow, into the second column.

13. Method according to claim 9,
wherein the low-boiling impurities removed at the head of the first column are furthermore condensed in a condenser and returned, at least in part, into the first column as a return flow.

14. Method according to claim 10,
wherein a ratio of the concentration of the high-boiling impurities in the bottom of the second column during operation of the facility, relative to the initial concentration in the recovered NMP, is approximately 1-5, and a ratio of the concentration of the high-boiling impurities in the lower part of the first column is increased relative to this value and is in the range of greater than 1 to approximately 100.

* * * * *